(12) United States Patent
Coulomb et al.

(10) Patent No.: US 10,980,722 B2
(45) Date of Patent: Apr. 20, 2021

(54) LILY OF THE VALLEY ODORANT

(71) Applicant: FIRMENICH SA, Satigny (CH)

(72) Inventors: Julien Coulomb, Satigny (CH); Gilles Oddon, Satigny (CH)

(73) Assignee: FIRMENICH SA, Satigny (CH)

(*) Notice: Subject to any disclaimer, the term of this patent is extended or adjusted under 35 U.S.C. 154(b) by 0 days.

(21) Appl. No.: 16/757,955

(22) PCT Filed: Jan. 17, 2019

(86) PCT No.: PCT/EP2019/051112
§ 371 (c)(1),
(2) Date: Apr. 21, 2020

(87) PCT Pub. No.: WO2019/141761
PCT Pub. Date: Jul. 25, 2019

(65) Prior Publication Data
US 2020/0337962 A1    Oct. 29, 2020

(30) Foreign Application Priority Data
Jan. 19, 2018  (EP) .................................. 18152452

(51) Int. Cl.
| A61K 8/18 | (2006.01) |
| A61Q 13/00 | (2006.01) |
| A61K 8/00 | (2006.01) |
| A61K 8/34 | (2006.01) |
| A61Q 19/00 | (2006.01) |

(52) U.S. Cl.
CPC ............... *A61K 8/34* (2013.01); *A61Q 19/00* (2013.01)

(58) Field of Classification Search
USPC ................. 512/20, 17, 16, 14, 8, 1
See application file for complete search history.

(56) References Cited

U.S. PATENT DOCUMENTS

| 4,396,670 | A | 8/1983 | Sinclair | |
| 2018/0201873 | A1* | 7/2018 | Coulomb | .................. A61K 8/34 |
| 2019/0249111 | A1* | 8/2019 | Walther | .................. C11B 9/0061 |
| 2019/0276769 | A1* | 9/2019 | Saudan | .................. C07C 45/505 |

FOREIGN PATENT DOCUMENTS

| WO | 0141915 A1 | 6/2001 | |
| WO | 2016074719 A1 | 5/2016 | |
| WO | 2017009175 A1 | 1/2017 | |
| WO | WO-2017009175 A1 * | 1/2017 | ............. A61Q 13/00 |

OTHER PUBLICATIONS

International Search Report and Written Opinion for corresponding PCT/EP2019/051112, dated Feb. 28, 2019, 12 Pages.
Dietrich, K. et al., Amino resin microcapsules, Acta Polymerica, 1989, pp. 243-251, vol. 40, No. 4.
Dietrich, K. et al., Amino resin microcapsules, Acta Polymerica, 1989, pp. 325-331, vol. 40, No. 5.
Dietrich, K. et al., Amino resin microcapsules, Acta Polymerica, 1989, pp. 683-690, vol. 40, No. 11.
Dietrich, K. et al., Amino resin microcapsules, Acta Polymerica, 1990, pp. 91-95, vol. 41, No. 2.
Lee, H. Y. et al., Microencapsulation of fragrant oil via in situ polymerization: effects of pH and melamineformaldehyde molar ratio, Journal of Microencapsulation, 2002, pp. 559-569, vol. 19, No. 5.
Bône S. et al. Microencapsulated Fragrances in Melamine Formaldehyde Resins, CHIMIA, 2011, pp. 177-181, vol. 65, No. 3.

\* cited by examiner

*Primary Examiner* — Jessica Whiteley
(74) *Attorney, Agent, or Firm* — Armstrong Teasdale LLP

(57) ABSTRACT

The present disclosure concerns a perfuming ingredient of a compound of formula (I)

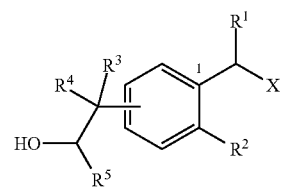

in the form of any one of its stereoisomers or a mixture thereof, and wherein X represents a CHO group when R1 represents a C1-2 alkyl group or X represents a CH(R6) CHO group when R1 represents a hydrogen atom or a C1-2 alkyl group. Each of R2, R3, R4, R5 and R6 represents, independently from each other, a hydrogen atom or a C1-2 alkyl group; or R3 and R4 represent, when taken together, a ethanediyl group; and —C(R3)(R4)—CH(R5)—OH group is, relative to position 1, an ortho, a meta, a para substituent of the aromatic ring or a mixture thereof. Also disclosed is the compound of formula (I) as part of a perfuming composition or of a perfumed consumer product.

17 Claims, No Drawings

LILY OF THE VALLEY ODORANT

This application is a U.S. National Phase Application of PCT/EP2019/051112, filed Jan. 17, 2019, which claims priority to EP Application No. 18152452.1, filed on Jan. 19, 2018, the contents of which are hereby incorporated by reference in their entirety.

TECHNICAL FIELD

The present invention relates to the field of perfumery. More particularly, it concerns the use as perfuming ingredient of a compound of formula (I), as defined below, in particular to confer odor notes of Lyral® type. Moreover, following what is mentioned herein, the present invention comprises the compound of formula (I) as part of a perfuming composition or of a perfuming consumer product.

BACKGROUND

One of the key ingredients in the perfumery industry are the one imparting a floral impression and in particular a lily of the valley odor. Said note is very appreciated and used in a multitude of perfumed consumer products. Lilial® (2-methyl-3-[4-(2-methyl-2-propanyl)phenyl]propanal, trademark from Givaudan-Roure SA, Vernier, Suisse) and Lyral® (4/3-(4-hydroxy-4-methylpentyl)-3-cyclohexene-1-carbaldehyde; origin International Flavors & Fragrances, USA) are both common ingredients use in this goal. Lilial® possesses lily of the valley and watery connotation while Lyral® imparts floral, lily of the valley, hydroxycitronellal odor notes quite different from the notes of Lilial®. However, both ingredients have been limited due to various reasons So, there is a need to develop novel perfuming ingredients imparting lily of valley which could be used as Lilial® or Lyral® replacers.

All hydroxyaldehyde Lyral® replacers developed have maintained the tertiary alcohol functional group present in Lyral®.

To the best of our knowledge, the present invention discloses for the first time a perfuming hydroxyaldehyde compound which could be used to substitute Lyral® while not comprising the typical tertiary alcohol functional group. Only one closely related structural analogue of compound of formula (I) has been reported in WO 2017009175 as perfuming ingredient characterizing by having a nice and well balanced floral, lily of the valley, hydroxycitronellal odor note, and an overall olfactive character reminding strongly of the one of the very well-known ingredient Lyral. Said analogues being 3-[4-(2-hydroxy-2-methylpropyl)phenyl] propanal possesses as Lyral® a tertiary alcohol, i.e. a totally different chemical structure from the present invention's compound.

The prior art document does not report or suggest any organoleptic properties of the compound of formula (I), or any use of said compounds in the field of perfumery.

SUMMARY OF THE INVENTION

The invention relates to compound of formula (I) which could be used to impart floral-muguet note in the direction of Lyral®.

So, a first object of the present invention is a compound of formula

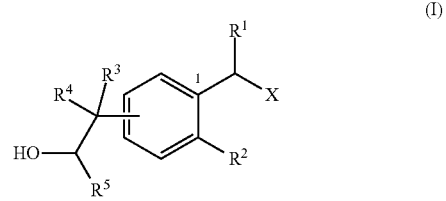

in the form of any one of its stereoisomers or a mixture thereof, and wherein

X represents a CHO group when $R^1$ represents a $C_{1-2}$ alkyl group or X represents a $CH(R^6)CHO$ group when $R^1$ represents a hydrogen atom or a $C_{1-2}$ alkyl group;

each $R^2$, $R^3$, $R^4$, $R^5$ and $R^6$ represents, independently from each other, a hydrogen atom or a $C_{1-2}$ alkyl group; or $R^3$ and $R^4$ represent, when taken together, an ethanediyl group; and —$C(R^3)(R^4)$—$CH(R^5)$—OH group is, relative to position 1, an ortho, a meta, a para substituent of the aromatic ring or a mixture thereof.

A second object of the present invention is a method to confer, enhance, improve or modify the odor properties of a perfuming composition or of a perfumed article, which method comprises adding to said composition or article an effective amount of at least a compound of formula (I) as defined above.

A third object of the present invention is a compound of formula (I) as defined above provided that 3-(4-(1-hydroxy-2-methylpropan-2-yl)phenyl)propanal, 3-(4-(2-hydroxyethyl)phenyl)propanal, 3-(4-(1-(hydroxymethyl)cyclopropyl)phenyl)propanal, 3-(4-(1-hydroxy-2-methylpropan-2-yl)phenyl)butanal, 3-(4-(2-hydroxypropyl)phenyl)propanal, 3-(4-(1-(hydroxymethyl)cyclopropyl)phenyl)butanal, 3-(3-(1-(hydroxymethyl)cyclopropyl)phenyl)butanal, 3-(3-(1-(hydroxymethyl)cyclopropyl)phenyl)propanal, 3-(2-(1-(hydroxymethyl)cyclopropyl)phenyl)propanal, 3-(2-(1-(hydroxymethyl)cyclopropyl)phenyl)butanal, 3-(3-(2-hydroxypropyl)phenyl)butanal, 3-(3-(2-hydroxypropyl)phenyl)propanal, 3-(3-(2-hydroxyethyl)phenyl)propanal, 3-(3-(2-hydroxyethyl)phenyl)butanal, 3-(3-(1-hydroxy-2-methylpropan-2-yl)phenyl)butanal, 3-(3-(1-hydroxy-2-methylpropan-2-yl)phenyl)propanal, 3-(2-(1-hydroxy-2-methylpropan-2-yl)phenyl)propanal, 3-(2-(1-hydroxy-2-methylpropan-2-yl)phenyl)butanal, 3-(2-(2-hydroxypropyl)phenyl)butanal, 3-(2-(2-hydroxypropyl)phenyl)propanal, 3-(4-(2-hydroxyethyl)phenyl)butanal and 3-(4-(2-hydroxypropyl)phenyl)butanal are excluded.

Another object of the present invention is a perfuming composition comprising i) at least one compound of formula (I), as defined above;
ii) at least one ingredient selected from the group consisting of a perfumery carrier and a perfumery base; and
iii) optionally at least one perfumery adjuvant.

A last object of the present invention is a perfumed consumer product comprising at least one compound of formula (I), as defined above or a composition as defined above.

DESCRIPTION OF THE INVENTION

Surprisingly, it has now been discovered that a compound of formula (I), possessing a primary or secondary alcohol functional group, imparts an odor note very interesting of the lily of the valley type which is very closed to the overall olfactive character of Lyral® while conferring in addition powdery connotation which is particularly appreciated. The combination of both notes is very rare.

Surprisingly, it has now been discovered that a compound of formula

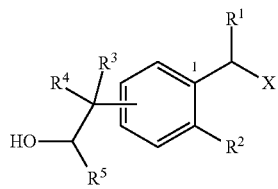

(I)

in the form of any one of its stereoisomers or a mixture thereof, and wherein

X represents a CHO group when $R^1$ represents a $C_{1-2}$ alkyl group or X represents a $CH(R^6)CHO$ group when $R^1$ represents a hydrogen atom or a $C_{1-2}$ alkyl group;

each $R^2$, $R^3$, $R^4$, $R^5$ and $R^6$ represents, independently from each other, a hydrogen atom or a $C_{1-2}$ alkyl group; or $R^3$ and $R^4$ represent, when taken together, a ethanediyl group; and —$C(R^3)(R^4)$—$CH(R^5)$—OH group is, relative to position 1, an ortho, a meta, a para substituent of the aromatic ring or a mixture thereof;

can be used as perfuming ingredient, for instance to impart in addition to odor notes of the Lyral® type also powdery note.

For the sake of clarity, by the expression "any one of its stereoisomers", or the similar, it is meant the normal meaning understood by a person skilled in the art, i.e. that the invention's compound can be a pure enantiomer (if chiral), a mixture of enantiomers, a pure diastereomer, a mixture of diastereoisomers; or a mixture thereof.

For the sake of clarity, by the expression "—$C(R^3)(R^4)$—$CH(R^5)$—OH group is, relative to position 1, an ortho, a meta, a para substituent of the aromatic ring or a mixture thereof", it designates that the compound of formula (I) may be in the form of a pure regioisomer; e.g. —$C(R^3)(R^4)$—$CH(R^5)$—OH group being a para substituent of the aromatic ring, relative to position 1 or the compound of formula (I) may be in the form of a mixture of regioisomers; e.g. a mixture comprising a compound of formula (I) wherein —$C(R^3)(R^4)$—$CH(R^5)$—OH group is a para substituent of the aromatic ring, relative to position 1 and a compound of formula (I) wherein —$C(R^3)(R^4)$—$CH(R^5)$—OH group is a meta substituent of the aromatic ring, relative to position 1. When compound of formula (I) is in the form of a mixture of regioisomers, X, $R^1$, $R^2$, $R^3$, $R^4$, $R^5$ and $R^6$ have the same meaning in each regioisomer.

According to any one of the above embodiments of the invention, said compounds (I) are $C_{11}$-$C_{18}$ compounds, preferably a $C_{11}$-$C_{15}$.

According to any one of the above embodiments, the —$C(R^3)(R^4)$—$CH(R^5)$—OH group may be a meta or para substituent of the aromatic ring, relative to position 1.

According to any one of the above embodiments, the compound used as perfuming ingredient is a compound of formula

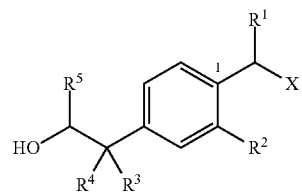

(II)

in the form of any one of its stereoisomers or a mixture thereof, and wherein X, $R^1$, $R^2$, $R^3$, $R^4$, $R^5$ and $R^6$ have the same meaning as above.

According to any one of the above embodiments, the compound used as perfuming ingredient is a compound of formula

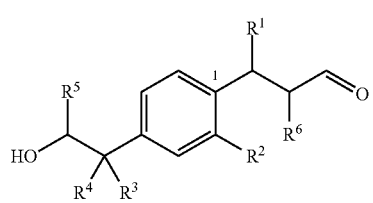

(III)

in the form of any one of its stereoisomers or a mixture thereof, and wherein $R^1$, $R^2$, $R^3$, $R^4$, $R^5$ and $R^6$ have the same meaning as above.

According to any one of the above embodiments, the compound used as perfuming ingredient is a compound of formula

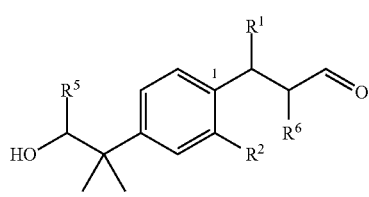

(IV)

in the form of any one of its stereoisomers or a mixture thereof, and wherein $R^1$, $R^2$, $R^3$, $R^4$, $R^5$ and $R^6$ have the same meaning as above.

According to any one of the above embodiments of the invention, $R^1$, $R^2$, $R^3$, $R^4$, $R^5$ and $R^6$, independently from each other may be a hydrogen atom or a methyl group; or $R^3$ and $R^4$ represent, when taken together, an ethanediyl group. In particular, one or two of said $R^1$, $R^2$, $R^3$, $R^4$, $R^5$ and $R^6$ may represent a hydrogen atom, and others a hydrogen atom or a methyl group.

According to any one of the above embodiments of the invention, $R^1$ may be a $C_1$-$C_2$ alkyl group when X represents a CHO group or $R^1$ may be a hydrogen atom or a $C_{1-2}$ alkyl group when X represents a $CH(R^6)CHO$ group and $R^6$ has the same meaning as defined above. Preferably, $R^1$ may be methyl group when X represents a CHO group or $R^1$ may be a hydrogen atom or a methyl group when X represents a $CH(R^6)CHO$ group. Even more preferably, $R^1$ may be methyl group when X represents a CHO group or $R^1$ may be a hydrogen atom when X represents a $CH(R^6)CHO$ group. Even more preferably, $R^1$ may be a hydrogen atom and X represents a $CH(R^6)CHO$ group.

According to any one of the above embodiments of the invention, $R^2$ may be a hydrogen atom or a $C_{1-2}$ alkyl group. Preferably, $R^2$ may be a hydrogen atom or a methyl group. Even more preferably, $R^2$ may be a hydrogen atom.

According to any one of the above embodiments of the invention, $R^5$ may be a hydrogen atom or a $C_{1-2}$ alkyl group. Preferably, $R^5$ may be a hydrogen atom or a methyl group. Even more preferably, $R^5$ may be a hydrogen atom.

According to any one of the above embodiments of the invention, $R^6$ may be a hydrogen atom or a $C_{1-2}$ alkyl group. Preferably, $R^6$ may be a hydrogen atom or a methyl group. Even more preferably, $R^6$ may be a hydrogen atom.

According to any one of the above embodiments of the invention, $R^3$ and $R^4$ may be a hydrogen atom or a $C_{1-2}$ alkyl group; or $R^3$ and $R^4$ may represent, when taken together, an ethanediyl group. Preferably, $R^3$ and $R^4$ may be a hydrogen atom or a methyl group; or $R^3$ and $R^4$ may represent, when taken together, an ethanediyl group. Preferably, $R^3$ may be a methyl group and $R^4$ may be a hydrogen atom or a methyl group; or $R^3$ and $R^4$ may represent, when taken together, an ethanediyl group. Preferably, $R^3$ and $R^4$ may represent a methyl group or $R^3$ and $R^4$ may represent, when taken together, a ethanediyl group. Even more preferably, $R^3$ and $R^4$ may represent a methyl group.

According to any one of the above embodiments of the invention, the compound of formula (I) may be selected from the group consisting of 3-(4-(1-hydroxy-2-methylpropan-2-yl)phenyl)propanal, 3-(4-(1-hydroxy-2-methylpropan-2-yl)phenyl)-2-methylpropanal, 3-(4-(2-hydroxyethyl)phenyl)propanal, 3-(4-(1-hydroxypropan-2-yl)phenyl)propanal, 3-(4-(1-(hydroxymethyl)cyclopropyl)phenyl)propanal, 3-(4-(1-hydroxy-2-methylpropan-2-yl)phenyl)butanal, 3-(4-(2-hydroxypropyl)phenyl)propanal, 3-(4-(3-hydroxy-2-methylbutan-2-yl)phenyl)propanal, 3-(4-(3-hydroxybutan-2-yl)phenyl)propanal and 3-(4-(1-hydroxy-2-methylpropan-2-yl)-2-methylphenyl)propanal. Preferably, the invention's compound may be selected from the group consisting of 3-(4-(1-hydroxy-2-methylpropan-2-yl)phenyl)propanal, 3-(4-(1-hydroxy-2-methylpropan-2-yl)phenyl)-2-methylpropanal, 3-(4-(1-hydroxypropan-2-yl)phenyl)propanal, 3-(4-(2-hydroxypropyl)phenyl)propanal, 3-(4-(3-hydroxybutan-2-yl)phenyl)propanal and 3-(4-(1-hydroxy-2-methylpropan-2-yl)-2-methylphenyl)propanal. Even more preferably, the invention's compound may be selected from the group consisting of 3-(4-(1-hydroxy-2-methylpropan-2-yl)phenyl)propanal, 3-(4-(1-hydroxy-2-methylpropan-2-yl)phenyl)-2-methylpropanal, 3-(4-(1-hydroxypropan-2-yl)phenyl)propanal, 3-(4-(2-hydroxypropyl)phenyl)propanal and 3-(4-(3-hydroxybutan-2-yl)phenyl)propanal. Even more preferably, the invention's compound may be 3-(4-(1-hydroxy-2-methylpropan-2-yl)phenyl)propanal, 3-(4-(2-hydroxypropyl)phenyl)propanal and 3-(4-(3-hydroxybutan-2-yl)phenyl)propanal. Even more preferably, the invention's compound may be 3-(4-(1-hydroxy-2-methylpropan-2-yl)phenyl)propanal.

To the best of our knowledge, the compounds of formula (I) as herein above reported are novel, and therefore also an object of the present invention provided that 3-(4-(1-hydroxy-2-methylpropan-2-yl)phenyl)propanal, 3-(4-(2-hydroxyethyl)phenyl)propanal, 3-(4-(1-(hydroxymethyl)cyclopropyl)phenyl)propanal, 3-(4-(1-hydroxy-2-methylpropan-2-yl)phenyl)butanal, 3-(4-(2-hydroxypropyl)phenyl)propanal, 3-(4-(1-(hydroxymethyl)cyclopropyl)phenyl)butanal, 3-(3-(1-(hydroxymethyl)cyclopropyl)phenyl)butanal, 3-(3-(1-(hydroxymethyl)cyclopropyl)phenyl)propanal, 3-(2-(1-(hydroxymethyl)cyclopropyl)phenyl)propanal, 3-(2-(1-(hydroxymethyl)cyclopropyl)phenyl)butanal, 3-(3-(2-hydroxypropyl)phenyl)butanal, 3-(3-(2-hydroxypropyl)phenyl)propanal, 3-(3-(2-hydroxyethyl)phenyl)propanal, 3-(3-(2-hydroxyethyl)phenyl)butanal, 3-(3-(1-hydroxy-2-methylpropan-2-yl)phenyl)butanal, 3-(3-(1-hydroxy-2-methylpropan-2-yl)phenyl)propanal, 3-(2-(1-hydroxy-2-methylpropan-2-yl)phenyl)propanal, 3-(2-(1-hydroxy-2-methylpropan-2-yl)phenyl)butanal, 3-(2-(2-hydroxypropyl)phenyl)butanal, 3-(2-(2-hydroxypropyl)phenyl)propanal, 3-(4-(2-hydroxyethyl)phenyl)butanal and 3-(4-(2-hydroxypropyl)phenyl)butanal are excluded.

As specific examples of the compound of formula (I), one may cite, as non-limiting example, 3-(4-(1-hydroxy-2-methylpropan-2-yl)phenyl)propanal which is characterized by having a floral, lily of the valley odor note, and an overall olfactive character reminding strongly of the one of the very well-known ingredient Lyral® (4/3-(4-hydroxy-4-methylpentyl)-3-cyclohexene-1-carbaldehyde; origin International Flavors & Fragrances, USA). This striking resemblance is of high interest for the industry since Lyral® is now limited in use for allergen reasons and the industry is still waiting for olfactive substitutes for this ingredient. In addition, said ingredient also possesses powdery and creamy note which bend particularly well with musky notes.

According to a particular embodiment of the invention, the compounds of formula (I) are 3-(4-(1-hydroxy-2-methylpropan-2-yl)phenyl)propanal.

When the odor of the invention's compound is compared with that of the prior art compound 3-[4-(2-hydroxy-2-methylpropyl)phenyl]propanal, then the invention's compound also possesses lily of the valley odor note of the Lyral® type but distinguishes themselves by a powdery note. The invention's compound contrary to the prior art compound harmonizes very well with salicate and musky note. The invention's compound may be use as a Lyral® replacer while bringing in addition a powdery/creamy note boosting the musk note of a composition. Said differences lend the invention's compounds and the prior art compounds to be each suitable as a Lyral® replacer but in two different uses, i.e. to impart different organoleptic impressions.

As mentioned above, the invention concerns the use of a compound of formula (I) as a perfuming ingredient. In other words, it concerns a method or a process to confer, enhance, improve or modify the odor properties of a perfuming composition or of a perfumed article or of a surface, which method comprises adding to said composition or article an effective amount of at least a compound of formula (I), e.g. to impart its typical note. Understood that the final hedonic effect may depend on the precise dosage and on the organoleptic properties of the invention's compound, but anyway the addition of the invention's compound will impart to the final product its typical touch in the form of a note, touch or aspect depending on the dosage.

By "use of a compound of formula (I)" it has to be understood here also the use of any composition containing a compound (I) and which can be advantageously employed in the perfumery industry.

Said compositions, which in fact can be advantageously employed as perfuming ingredients, are also an object of the present invention.

Therefore, another object of the present invention is a perfuming composition comprising:
i) as a perfuming ingredient, at least one invention's compound as defined above;
ii) at least one ingredient selected from the group consisting of a perfumery carrier and a perfumery base; and
iii) optionally at least one perfumery adjuvant.

By "perfumery carrier" it is meant here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples, solvents such as butylene or propylene glycol, glycerol, dipropyleneglycol and its monoether, 1,2,3-propanetriyl triacetate, dimethyl glutarate, dimethyl adipate 1,3-diacetyloxypropan-2-yl acetate, diethyl phthalate, isopropyl myristate, benzyl benzoate, benzyl alcohol, 2-(2-ethoxyethoxy)-1-ethano, tri-ethyl citrate or mixtures thereof, which are the most commonly used. For the compositions which comprise both a perfumery carrier and a perfumery base, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company), or hydrogenated castors oils such as those known under the trademark Cremophor® RH 40 (origin: BASF).

Solid carrier is meant to designate a material to which the perfuming composition or some element of the perfuming composition can be chemically or physically bound. In general such solid carriers are employed either to stabilize the composition, or to control the rate of evaporation of the compositions or of some ingredients. The use of solid carrier is of current use in the art and a person skilled in the art knows how to reach the desired effect. However by way of non-limiting example of solid carriers, one may cite absorbing gums or polymers or inorganic material, such as porous polymers, cyclodextrins, wood based materials, organic or inorganic gels, clays, gypsum talc or zeolites.

As other non-limiting examples of solid carriers, one may cite encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs- and Geliermittel in Lebensmitteln, Band 2 der Schriftenreihe Lebensmittelchemie, Lebensmittelqualität, Behr's Verlag GmbH & Co., Hamburg, 1996. The encapsulation is a well-known process to a person skilled in the art, and may be performed, for instance, by using techniques such as spray-drying, agglomeration or yet extrusion; or consists of a coating encapsulation, including coacervation and complex coacervation technique.

As non-limiting examples of solid carriers, one may cite in particular the core-shell capsules with resins of aminoplast, polyamide, polyester, polyurea or polyurethane type or a mixture thereof (all of said resins are well known to a person skilled in the art) using techniques like phase separation process induced by polymerization, interfacial polymerization, coacervation or altogether (all of said techniques have been described in the prior art), optionally in the presence of a polymeric stabilizer or of a cationic copolymer.

Resins may be produced by the polycondensation of an aldehyde (e.g. formaldehyde, 2,2-dimethoxyethanal, glyoxal, glyoxylic acid or glycolaldehyde and mixtures thereof) with an amine such as urea, benzoguanamine, glycoluryl, melamine, methylol melamine, methylated methylol melamine, guanazole and the like, as well as mixtures thereof. Alternatively one may use preformed resins alkylolated polyamines such as those commercially available under the trademark Urac® (origin: Cytec Technology Corp.), Cymel® (origin: Cytec Technology Corp.), Urecoll® or Luracoll® (origin: BASF).

Others resins one are the ones produced by the polycondensation of an a polyol, like glycerol, and a polyisocyanate, like a trimer of hexamethylene diisocyanate, a trimer of isophorone diisocyanate or xylylene diisocyanate or a Biuret of hexamethylene diisocyanate or a trimer of xylylene diisocyanate with trimethylolpropane (known with the tradename of Takenate®, origin: Mitsui Chemicals), among which a trimer of xylylene diisocyanate with trimethylolpropane and a Biuret of hexamethylene diisocyanate.

Some of the seminal literature related to the encapsulation of perfumes by polycondensation of amino resins, namely melamine based resins with aldehydes includes represented by articles such as those published by K. Dietrich et al. Acta Polymerica, 1989, vol. 40, pages 243, 325 and 683, as well as 1990, vol. 41, page 91. Such articles already describe the various parameters affecting the preparation of such core-shell microcapsules following prior art methods that are also further detailed and exemplified in the patent literature. U.S. Pat. No. 4,396,670, to the Wiggins Teape Group Limited is a pertinent early example of the latter. Since then, many other authors have enriched the literature in this field and it would be impossible to cover all published developments here, but the general knowledge in encapsulation technology is very significant. More recent publications of pertinency, which disclose suitable uses of such microcapsules, are represented for example by the article of H. Y. Lee et al. Journal of Microencapsulation, 2002, vol. 19, pages 559-569, international patent publication WO 01/41915 or yet the article of S. Bône et al. Chimia, 2011, vol. 65, pages 177-181.

By "perfumery base" what is meant here is a composition comprising at least one perfuming co-ingredient.

Said perfuming co-ingredient is not of formula (I). Moreover, by "perfuming co-ingredient" it is meant here a compound, which is used in a perfuming preparation or a composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of his general knowledge and according to the intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin.

In particular one may cite perfuming co-ingredients knows for having a similar olfactive note, such as:

In particular one may cite perfuming co-ingredients which are commonly used in perfume formulations, such as:

Aldehydic ingredients: decanal, dodecanal, 2-methyl-undecanal, 10-undecenal, octanal and/or nonenal;

Aromatic-herbal ingredients: eucalyptus oil, camphor, eucalyptol, menthol and/or alpha-pinene;

Balsamic ingredients: coumarine, ethylvanillin and/or vanillin;

Citrus ingredients: dihydromyrcenol, citral, orange oil, linalyl acetate, citronellyl nitrile, orange terpenes, limonene, 1-P-menthen-8-yl acetate and/or 1,4(8)-P-menthadiene;

Floral ingredients: Methyl dihydrojasmonate, linalool, citronellol, phenylethanol, 3-(4-tert-butylphenyl)-2-methylpropanal, hexylcinnamic aldehyde, benzyl acetate, benzyl salicylate, tetrahydro-2-isobutyl-4-methyl-4(2H)-pyranol, beta ionone, methyl 2-(methylamino)benzoate, (E)-3-methyl-4-(2,6,6-trimethyl-2-cyclohexen-1-yl)-3-buten-2-one, hexyl salicylate, 3,7-dimethyl-1,6-nonadien-3-ol, 3-(4-isopropylphenyl)-2-methylpropanal, verdyl acetate, geraniol, P-menth-1-en-8-ol, 4-(1,1-dimethylethyl)-1-cyclohexyle acetate, 1,1-dimethyl-2-phenylethyl acetate, 4-cyclohexyl-2-methyl-2-butanol, amyl salicylate, high cis methyl dihydrojasmonate, 3-methyl-5-phenyl-1-pentanol, verdyl proprionate, geranyl acetate, tetrahydro linalool, cis-7-P-menthanol, Propyl (S)-2-(1,1-dimethylpropoxy)propanoate, 2-methoxynaphthalene, 2,2,2-trichloro-1-phenylethyl acetate, 4/3-(4-hydroxy-4-methylpentyl)-3-cyclohexene-1-carbaldehyde, amylcinnamic aldehyde, 4-phenyl-2-butanone, isononyle acetate, 4-(1,1-dimethylethyl)-1-cyclohexyl acetate, verdyl isobutyrate and/or mixture of methyl-ionones isomers;

Fruity ingredients: gamma undecalactone, 4-decanolide, ethyl 2-methyl-pentanoate, hexyl acetate, ethyl 2-methylbutanoate, gamma nonalactone, allyl heptanoate, 2-phenoxyethyl isobutyrate, ethyl 2-methyl-1,3-dioxolane-2-acetate and/or diethyl 1,4-cyclohexane dicarboxylate;

Green ingredients: 2,4-dimethyl-3-cyclohexene-1-carbaldehyde, 2-tert-butyl-1-cyclohexyl acetate, styrallyl acetate, allyl (2-methylbutoxy)acetate, 4-methyl-3-decen-5-ol, diphenyl ether, (Z)-3-hexen-1-ol and/or 1-(5,5-dimethyl-1-cyclohexen-1-yl)-4-penten-1-one;

Musk ingredients: 1,4-dioxa-5,17-cycloheptadecanedione, pentadecenolide, 3-methyl-5-cyclopentadecen-1-one, 1,3,4,6,7,8-hexahydro-4,6,6,7,8,8-hexamethylcyclopenta-g-2-benzopyrane, (1S,1'R)-2-[1-(3',3'-dimethyl-1'-cyclohexyl)ethoxy]-2-methylpropyl propanoate, pentadecanolide and/or (1S,1R)-[1-(3',3'-Dimethyl-1'-cyclohexyl)ethoxycarbonyl]methyl propanoate;

Woody ingredients: 1-(octahydro-2,3,8,8-tetramethyl-2-naphtalenyl)-1-ethanone, patchouli oil, terpenes fractions of patchouli oil, (1'R,E)-2-ethyl-4-(2',2',3'-trimethyl-3'-cyclopenten-1'-yl)-2-buten-1-ol, 2-ethyl-4-(2,2,3-trimethyl-3-cyclopenten-1-yl)-2-buten-1-ol, Methyl cedryl ketone, 5-(2,2,3-trimethyl-3-cyclopentenyl)-3-methylpentan-2-ol, 1-(2,3,8,8-tetramethyl-1,2,3,4,6,7,8,8a-octahydronaphthalen-2-yl)ethan-1-one and/or isobornyl acetate;

Other ingredients (e.g. amber, powdery spicy or watery): dodecahydro-3a,6,6,9a-tetramethyl-naphtho[2,1-b]furan and any of its stereoisomers, heliotropin, anisic aldehyde, eugenol, cinnamic aldehyde, clove oil, 3-(1,3-benzodioxol-5-yl)-2-methylpropanal and/or 3-(3-isopropyl-1-phenyl)butanal.

A perfumery base according to the invention may not be limited to the above mentioned perfuming co-ingredients, and many other of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant" we mean here an ingredient capable of imparting additional added benefit such as a color, a particular light resistance, chemical stability, etc. A detailed description of the nature and type of adjuvant commonly used in perfuming composition cannot be exhaustive, but it has to be mentioned that said ingredients are well known to a person skilled in the art. One may cite as specific non-limiting examples the following: viscosity agents (e.g. surfactants, thickeners, gelling and/or rheology modifiers), stabilizing agents (e.g. preservatives, antioxidant, heat/light and or buffers or chelating agents, such as BHT), coloring agents (e.g. dyes and/or pigments), preservatives (e.g. antibacterial or antimicrobial or antifungal or anti irritant agents), abrasives, skin cooling agents, fixatives, insect repellants, ointments, vitamins and mixtures thereof.

It is understood that a person skilled in the art is perfectly able to design optimal formulations for the desired effect by admixing the above mentioned components of a perfuming composition, simply by applying the standard knowledge of the art as well as by trial and error methodologies.

An invention's composition consisting of at least one compound of formula (I) and at least one perfumery carrier consists of a particular embodiment of the invention as well as a perfuming composition comprising at least one compound of formula (I), at least one perfumery carrier, at least one perfumery base, and optionally at least one perfumery adjuvant.

According to a particular embodiment, the compositions mentioned above, comprise more than one compound of formula (I) and enable the perfumer to prepare accords or perfumes possessing the odor tonality of various compounds of the invention, creating thus new building block for creation purposes.

For the sake of clarity, it is also understood that any mixture resulting directly from a chemical synthesis, e.g. a reaction medium without an adequate purification, in which the compound of the invention would be involved as a starting, intermediate or end-product could not be considered as a perfuming composition according to the invention as far as said mixture does not provide the inventive compound in a suitable form for perfumery. Thus, unpurified reaction mixtures are generally excluded from the present invention unless otherwise specified.

The compound of formula (I) can also be advantageously used in all the fields of modern perfumery, i.e. fine or functional perfumery, to positively impart or modify the odor of a consumer product into which said compound (I) is added. Consequently, another object of the present invention consists of by a perfumed consumer product comprising, as a perfuming ingredient, at least one compound of formula (I), as defined above.

The compound of formula (I) can be added as such or as part of an invention's perfuming composition.

For the sake of clarity, "perfumed consumer product" is meant to designate a consumer product which delivers at least a pleasant perfuming effect to the surface or space to which it is applied (e.g. skin, hair, textile, or home surface). In other words, a perfumed consumer product according to the invention is a perfumed consumer product which comprises a functional formulation, as well as optionally additional benefit agents, corresponding to the desired consumer product, and an olfactive effective amount of at least one invention's compound. For the sake of clarity, said perfumed consumer product is a non-edible product.

The nature and type of the constituents of the perfumed consumer product do not warrant a more detailed description here, which in any case would not be exhaustive, the skilled person being able to select them on the basis of his general knowledge and according to the nature and the desired effect of said product.

Non-limiting examples of suitable perfumed consumer product include a perfume, such as a fine perfume, a splash or eau de parfum, a cologne or a shave or after-shave lotion; a fabric care product, such as a liquid or solid detergent, a fabric softener, a liquid or solid scent booster, a fabric refresher, an ironing water, a paper, a bleach, a carpet cleaner, a curtain-care product; a body-care product, such as a hair care product (e.g. a shampoo, a coloring preparation or a hair spray, a color-care product, a hair shaping product, a dental care product), a disinfectant, an intimate care product; a cosmetic preparation (e.g. a skin cream or lotion, a vanishing cream or a deodorant or antiperspirant (e.g. a spray or roll on), a hair remover, a tanning or sun or after sun product, a nail product, a skin cleansing, a makeup); or a skin-care product (e.g. a soap, a shower or bath mousse, oil or gel, or a hygiene product or a foot/hand care products); an air care product, such as an air freshener or a "ready to use" powdered air freshener which can be used in the home space (rooms, refrigerators, cupboards, shoes or car) and/or in a public space (halls, hotels, malls, etc.); or a home care product, such as a mold remover, a furnisher care product, a wipe, a dish detergent or a hard-surface (e.g. a floor, bath, sanitary or a window-cleaning) detergent; a leather care product; a car care product, such as a polish, a wax or a plastic cleaner.

Some of the above-mentioned perfumed consumer products may represent an aggressive medium for the invention's compounds, so that it may be necessary to protect the latter from premature decomposition, for example by encapsulation or by chemically binding it to another chemical which is suitable to release the invention's ingredient upon a suitable external stimulus, such as an enzyme, light, heat or a change of pH.

The proportions in which the compound of formula (I) can be incorporated into the various aforementioned products or compositions vary within a wide range of values. These values are dependent on the nature of the article to be perfumed and on the desired organoleptic effect as well as on the nature of the co-ingredients in a given base when the compounds according to the invention are mixed with perfuming co-ingredients, solvents or additives commonly used in the art.

For example, in the case of perfuming compositions, typical concentrations are in the order of 0.001% to 10% by weight, or even more, of the compounds of formula (I) based on the weight of the composition into which they are incorporated. In the case of perfumed consumer product, typical concentrations are in the order of 0.0001% to 2% by weight, preferably in the order of 0.0001% to 1% by weight, or even more, of the compounds of the formula (I) based on the weight of the consumer product into which they are incorporated.

The compound of formula (I) can be prepared according to a method as described herein-below.

EXAMPLES

The invention will now be described in further detail by way of the following examples, wherein the abbreviations have the usual meaning in the art, the temperatures are indicated in degrees centigrade (° C.); the NMR spectral data were recorded in $CDCl_3$ (if not stated otherwise) with a 500 MHz machine for $^1H$ and $^{13}C$, the chemical shifts δ are indicated in ppm with respect to TMS as standard, the coupling constants J are expressed in Hz.

Example 1

Synthesis of Compounds of Formula (I)

3-(4-(1-hydroxy-2-methylpropan-2-yl)phenyl)propanal

Step 1: 2-(4-bromophenyl)-2-methylpropan-1-ol

To a suspension of lithium aluminum hydride (2.95 g, 78 mmol, 2 equiv.) in THF (70 mL) at 0° C. was added a solution of methyl 2-(4-bromophenyl)-2-methylpropanoate (10 g, 39 mmol, 1 equiv.) in THF (60 mL) dropwise. After stirring at 0° C. for 1 h, the reaction was quenched sequentially with 3 mL of water, 9 mL of a 5% sodium hydroxide solution and 3 mL of water. It was filtered on a Celite pad using ether as an eluent. The solvent was evaporated and the residue was purified by bulb-to-bulb distillation (2-4 mbar, 130° C.) to afford 2-(4-bromophenyl)-2-methylpropan-1-ol (8.27 g, 93% yield).

$^1H$ NMR: 1.30 (s, 6H), 3.57 (s, 2H), 7.25 (d, J=8.6 Hz, 2H), 7.45 (d, J=8.6 Hz, 2H).

$^{13}C$ NMR: 145.6 (s), 131.4 (d, 2C), 128.2 (d, 2C), 120.1 (s), 72.8 (t), 39.9 (s), 25.2 (q, 2C).

Step 2: 3-(4-(1-hydroxy-2-methylpropan-2-yl)phenyl)propanal

A solution of 2-(4-bromophenyl)-2-methylpropan-1-ol (5.0 g, 21.8 mmol, 1 equiv.) and N-cyclohexyl-N-methylaminecyclohexanamine (5.5 mL, 24.0 mmol, 1.1 equiv.) in DMF (44 mL) was degassed and stirred under an argon atmosphere for 20 min. Allyl alcohol (1.63 mL, 24.0 mmol, 1.1 equiv.) and bis(dibenzylideneacetone)palladium(0) (125 mg, 0.22 mmol, 0.01 equiv.) were added, followed by 2-(tert-butylphosphino)-1-phenyl-1H-indole (221 mg, 0.66 mmol, 0.03 equiv.) and the reaction was heated to 100° C. for 1 h. After cooling down to r.t., it was diluted with ether and washed three times with water. The organic layer was dried over sodium sulfate and the solvent was evaporated. The residue (GC ratio of linear/branched products: 5.6:1) was purified by flash column chromatography on silica gel (Heptane/AcOEt 7:3 to 65:35) and bulb-to-bulb distillation (0.35 mbar, 140-145° C.) to afford the desired aldehyde as an oil (2.57 g, 57% yield).

$^1H$ NMR: 1.31 (s, 6H), 2.77 (t, J=7.5 Hz, 2H), 2.94 (t, J=7.5 Hz, 2H), 3.59 (s, 2H), 7.17 (d, J=8.3 Hz, 2H), 7.31 (d, J=8.3 Hz, 2H), 9.81 (t, J=1.4 Hz, 1H).

$^{13}C$ NMR: 201.7 (d), 144.4 (s), 138.1 (s), 128.3 (d, 2C), 126.5 (d, 2C), 73.0 (t), 45.2 (t), 39.8 (s), 27.5 (t), 25.3 (q, 2C).

Minor isomer: 2-(4-(1-hydroxy-2-methylpropan-2-yl)phenyl)propanal $^1H$ NMR: 1.33 (s, 6H), 1.44 (d, J=7.1 Hz, 3H), 3.61 (s, 2H), 3.62 (m, 1H), 7.19 (d, J=8.3 Hz, 2H), 7.40 (d, J=8.3 Hz, 2H), 9.67 (d, J=1.4 Hz, 1H).

$^{13}C$ NMR: 201.2 (d), 145.8 (s), 135.4 (s), 128.3 (d, 2C), 127.0 (d, 2C), 73.0 (t), 52.5 (d), 39.9 (s), 25.3 (q, 2C), 14.5 (q).

3-(4-(1-hydroxy-2-methylpropan-2-yl)phenyl)-2-methylpropanal

A solution of 2-(4-bromophenyl)-2-methylpropan-1-ol (2.0 g, 8.73 mmol, 1 equiv.) and N-cyclohexyl-N-methyl-aminecyclohexanamine (2.2 mL, 9.60 mmol, 1.1 equiv.) in DMF (17 mL) was degassed and stirred under an argon atmosphere for 20 min. Methallyl alcohol (0.81 mL, 9.60 mmol, 1.1 equiv.) and bis(dibenzylideneacetone)palladium (0) (50 mg, 0.087 mmol, 0.01 equiv.) were added, followed by 2-(tert-butylphosphino)-1-phenyl-1H-indole (88 mg, 0.26 mmol, 0.03 equiv.) and the reaction was heated to 100° C. for 1 h. After cooling down to r.t., it was diluted with ether and washed three times with water. The organic layer was dried over sodium sulfate and the solvent was evaporated. The residue was purified by flash column chromatography on silica gel (Heptane/AcOEt 7:3) and bulb-to-bulb distillation (0.35 mbar, 145-150° C.) to afford the desired aldehyde as an oil (1.49 g, 77% yield).

$^1$H NMR: 1.09 (d, J=7.0 Hz, 3H), 1.31 (s, 6H), 2.59 (A of ABX, J=13.8, 8.1 Hz, 1H), 2.67 (m, 1H), 3.06 (B of ABX, J=13.8, 6.1 Hz, 1H), 3.59 (s, 2H), 7.14 (d, J=8.3 Hz, 2H), 7.31 (d, J=8.3 Hz, 2H), 9.71 (d, J=1.6 Hz, 1H).

$^{13}$C NMR: 204.5 (d), 144.5 (s), 136.6 (s), 129.1 (d, 2C), 126.4 (d, 2C), 73.0 (t), 48.0 (d), 39.8 (s), 36.1 (t), 25.3 (q, 2C), 13.3 (q).

3-(4-(1-hydroxypropan-2-yl)phenyl)propanal

Step 1: ethyl 2-(4-bromophenyl)propanoate

To a solution of ethyl 2-(4-bromophenyl)acetate (17.1 g, 70 mmol, 1 equiv.) in THF (235 mL) at −78° C. was added a solution of lithium bis(trimethylsilyl)amide (1 M in THF, 77 mL, 77 mmol, 1.1 equiv.) dropwise. After stirring at −78° C. for 15 min, iodomethane (5.5 mL, 88 mmol, 1.25 equiv.) was added dropwise. After stirring at −78° C. for 1 h30, the reaction was quenched with a saturated solution of ammonium chloride. It was extracted three times with ether, the combined organic extracts were dried over sodium sulfate and the solvent was evaporated. The residue was purified by flash column chromatography on silica gel (Heptane/AcOEt 98:2) and bulb-to-bulb distillation (2-3 mbar, 140° C.) to afford the desired ester as an oil (9.72 g, 54% yield).

Step 2: 2-(4-bromophenyl)propan-1-ol

To a suspension of lithium aluminum hydride (1.42 g, 37 mmol, 2 equiv.) in THF (31 mL) at 0° C. was added a solution of ethyl 2-(4-bromophenyl)propanoate (4.8 g, 19 mmol, 1 equiv.) in THF (31 mL) dropwise. After stirring for 2 h at r.t., the reaction was cooled down to 0° C. and quenched successively with 1.4 mL of water, 4.2 mL of a 5% NaOH solution and 1.4 mL of water. It was filtered on a Celite pad using ether as an eluent and the solvent was evaporated. The crude product was used as such for the next step.

Step 3: 3-(4-(1-hydroxypropan-2-yl)phenyl)propanal

A solution of 2-(4-bromophenyl)propan-1-ol (3.78 g, 17.6 mmol, 1 equiv.) and N-cyclohexyl-N-methylaminecyclohexanamine (4.42 mL, 19.3 mmol, 1.1 equiv.) in DMF (35 mL) was degassed and stirred under an argon atmosphere for 20 min. Allyl alcohol (1.31 mL, 19.3 mmol, 1.1 equiv.) and bis(dibenzylideneacetone)palladium(0) (101 mg, 0.18 mmol, 0.01 equiv.) were added, followed by 2-(tert-butylphosphino)-1-phenyl-1H-indole (178 mg, 0.53 mmol, 0.03 equiv.) and the reaction was heated to 100° C. for 1 h. After cooling down to r.t., it was diluted with ether and washed three times with water. The organic layer was dried over sodium sulfate and the solvent was evaporated. The residue (GC ratio of linear/branched products: 5.6:1) was purified by flash column chromatography on silica gel (Heptane/AcOEt 6:4) and bulb-to-bulb distillation (0.35 mbar, 140-145° C.) to afford the desired aldehyde as an oil (1.92 g, 57% yield).

$^1$H NMR: 1.25 (d, J=7.0 Hz, 3H), 2.77 (dt, J=7.6, 1.3 Hz, 2H), 2.93 (t, J=7.6 Hz, 2H), 2.93 (m, 1H), 3.67 (d, J=6.8 Hz, 2H), 7.16 (m, 4H), 9.81 (t, J=1.3 Hz, 1H).

$^{13}$C NMR: 201.7 (d), 141.7 (s), 138.6 (s), 128.5 (d, 2C), 127.7 (d, 2C), 68.7 (t), 45.2 (t), 42.0 (d), 27.7 (t), 17.6 (q).

3-(4-(2-hydroxypropyl)phenyl)propanal

Step 1: 1-(4-bromophenyl)propan-2-ol

To a suspension of lithium aluminum hydride (891 mg, 23.5 mmol, 1 equiv.) in THF (30 mL) at 0° C. was added a solution of 1-(4-bromophenyl)propan-2-one (5.00 g, 23.5 mmol, 1 equiv.) in THF (17 mL) dropwise. After stirring at 0° C. for 1 h, the reaction was quenched sequentially with 0.9 mL of water, 2.7 mL of a 5% sodium hydroxide solution and 0.9 mL of water. It was filtered on a Celite pad using ether as an eluent. The solvent was evaporated and the residue was purified by bulb-to-bulb distillation (2-4 mbar, 130° C.) to afford 2-(4-bromophenyl)-2-methylpropan-1-ol (4.91 g, 97% yield).

$^1$H NMR: 1.22 (d, J=6.2 Hz, 3H), 2.65 (A of ABX, J=13.6, 7.8 Hz, 1H), 2.72 (B of ABX, J=13.6, 4.9 Hz, 1H), 3.98 (m, 1H), 7.08 (d, J=8.3 Hz, 2H), 7.42 (d, J=8.3 Hz, 2H).

$^{13}$C NMR (CDCl$_3$, 125 MHz): 137.5 (s), 131.6 (d, 2C), 131.1 (d, 2C), 120.3 (s), 68.7 (d), 45.0 (t), 22.9 (q).

Step 2: 3-(4-(2-hydroxypropyl)phenyl)propanal

A solution of 1-(4-bromophenyl)propan-2-ol (3.0 g, 13.9 mmol, 1 equiv.) and N-cyclohexyl-N-methylaminecyclohexanamine (3.5 mL, 15.3 mmol, 1.1 equiv.) in DMF (28 mL) was degassed and stirred under an argon atmosphere for 20 min. Allyl alcohol (1.04 mL, 15.3 mmol, 1.1 equiv.) and bis(dibenzylideneacetone)palladium(0) (80 mg, 0.14 mmol, 0.01 equiv.) were added, followed by 2-(tert-butylphosphino)-1-phenyl-1H-indole (141 mg, 0.42 mmol, 0.03 equiv.) and the reaction was heated to 100° C. for 1 h. After cooling down to r.t., it was diluted with ether and washed three times with water. The organic layer was dried over sodium sulfate and the solvent was evaporated. The residue (GC ratio of linear/branched products: 5.6:1) was purified by flash column chromatography on silica gel (Heptane/AcOEt 65:35) and bulb-to-bulb distillation (0.35 mbar, 140-145° C.) to afford the desired aldehyde as an oil (1.39 g, 52% yield).

$^1$H NMR: 1.23 (d, J=6.2 Hz, 3H), 2.66 (A of ABX, J=13.5, 7.9 Hz, 1H), 2.74 (B of ABX, J=13.5, 4.9 Hz, 1H), 2.77 (dt, J=7.6, 1.2 Hz, 2H), 2.93 (t, J=7.5 Hz, 2H), 3.99 (m, 1H), 7.14 (s, 4H), 9.81 (t, J=1.2 Hz, 1H).

$^{13}$C NMR: 201.6 (d), 138.4 (s), 136.5 (s), 129.6 (d, 2C), 128.5 (d, 2C), 68.8 (d), 45.3 (t), 45.2 (t), 27.7 (t), 22.8 (q).

3-(4-(3-hydroxybutan-2-yl)phenyl)propanal

Step 1: 3-(4-bromophenyl)butan-2-ol

To a solution of 1,4-dibromobenzene (15.0 g, 63.6 mmol, 1 equiv.) in THF (212 mL) at −78° C. was added n-BuLi (2.45 M, 26.0 mL, 63.6 mmol, 1 equiv.) dropwise. After stirring at −78° C. for 30 min, 2,3-dimethyloxirane (6.84 mL, 76 mmol, 1.2 equiv.) was added dropwise. After stirring at −78° C. for 30 min, boron trifluoride etherate (9.67 mL, 76 mmol, 1.2 equiv.) was added dropwise. After stirring at −78° C. for 2 h, the reaction was quenched with a 10% w/w solution of Na/K tartrates and the mixture was allowed to reach room temperature overnight. It was extracted three times with ether, the combined organic extracts were dried over sodium sulfate and the solvent was evaporated. The residue was purified by bulb-to-bulb distillation (125-130° C., 2-4 mbar) to afford 3-(4-bromophenyl)butan-2-ol as an oil (2.85 g, 20% yield).

Step 2: 3-(4-(3-hydroxybutan-2-yl)phenyl)propanal

A solution of 3-(4-bromophenyl)butan-2-ol (2.79 g, 12.2 mmol, 1 equiv.) and N-cyclohexyl-N-methylaminecyclohexanamine (3.07 mL, 13.4 mmol, 1.1 equiv.) in DMF (24 mL) was degassed and stirred under an argon atmosphere for 20 min. Allyl alcohol (0.91 mL, 13.4 mmol, 1.1 equiv.) and bis(dibenzylideneacetone)palladium(0) (70 mg, 0.12 mmol, 0.01 equiv.) were added, followed by 2-(tert-butylphosphino)-1-phenyl-1H-indole (123 mg, 0.36 mmol, 0.03 equiv.) and the reaction was heated to 100° C. for 1 h. After cooling down to r.t., it was diluted with ether and washed three times with water. The organic layer was dried over sodium sulfate and the solvent was evaporated. The residue (GC ratio of linear/branched products: 5.3:1) was purified by flash column chromatography on silica gel (Heptane/AcOEt 65:35) and bulb-to-bulb distillation (0.35 mbar, 140-145° C.) to afford the desired aldehyde as an oil (691 mg, 27% yield).
$^1$H NMR: 1.08 (d, J=6.3 Hz, 3H), 1.30 (d, J=7.0 Hz, 3H), 2.71 (s, 1H), 2.77 (dt, J=7.5, 1.3 Hz, 2H), 2.94 (t, J=7.6 Hz, 2H), 3.86 (m, 1H), 7.13 (s, 4H), 9.82 (t, J=1.3 Hz, 1H).
$^{13}$C NMR: 201.7 (d), 142.2 (s), 138.3 (s), 128.3 (d, 2C), 128.1 (d, 2C), 72.3 (d), 46.7 (d), 45.2 (t), 27.7 (t), 21.0 (q), 16.0 (q).

3-(4-(1-hydroxy-2-methylpropan-2-yl)-2-methylphenyl)propanal

Step 1: methyl 2-(4-bromo-3-methylphenyl)acetate

To a mixture of 2-(4-bromo-3-methylphenyl)acetic acid (10.0 g, 43.7 mmol, 1 equiv.) and potassium carbonate (9.05 g, 65.5 mmol, 1.5 equiv.) in acetone (87 mL) was added iodomethane (5.46 mL, 87 mmol, 2 equiv.) and the reaction was stirred at r.t. for 4 days. Acetone was evaporated, a saturated solution of ammonium chloride was added and it was extracted three times with ether. The combined organic extracts were dried over sodium sulfate and the solvent was evaporated. The residue was purified by bulb-to-bulb distillation (130-135° C., 2-4 mbar) to afford methyl 2-(4-bromo-3-methylphenyl)acetate as an oil (9.24 g, 87% yield).

Step 2: methyl 2-(4-bromo-3-methylphenyl)-2-methylpropanoate

To a solution of methyl 2-(4-bromo-3-methylphenyl)acetate (9.19 g, 37.8 mmol, 1 equiv.) in THF (126 mL) at −78° C. was added a solution of sodium bis(trimethylsilyl)amide (1 M in THF, 95 mL, 95 mmol, 2.3 equiv.) dropwise. After stirring at −78° C. for 15 min, methyl iodide (7.09 mL, 113 mL, 3 equiv.) was added dropwise. After stirring at −78° C. for 1 h30, the reaction was quenched with a saturated solution of ammonium chloride. It was extracted three times with ether, the combined organic extracts were dried over sodium sulfate and the solvent was evaporated. The residue was purified by flash column chromatography on silica gel (Heptane/AcOEt 98:2) and bulb-to-bulb distillation (2-3 mbar, 140° C.) to afford the desired ester as an oil (9.10 g, 89% yield).

Step 3: 2-(4-bromo-3-methylphenyl)-2-methylpropan-1-ol

To a suspension of lithium aluminum hydride (2.53 g, 66.8 mmol, 2 equiv.) in THF (60 mL) at 0° C. was added a solution of methyl 2-(4-bromo-3-methylphenyl)-2-methylpropanoate (9.05 g, 33.4 mmol, 1 equiv.) in THF (51 mL) dropwise. After stirring for 2 h at r.t., the reaction was cooled down to 0° C. and quenched successively with 2.5 mL of water, 7.5 mL of a 5% NaOH solution and 2.5 mL of water. It was filtered on a Celite pad using ether as an eluent and the solvent was evaporated. The crude product was used as such for the next step.

Step 4: 3-(4-(1-hydroxy-2-methylpropan-2-yl)-2-methylphenyl)propanal

A solution of 2-(4-bromo-3-methylphenyl)-2-methylpropan-1-ol (7.49 g, 27.1 mmol, 1 equiv.) and N-cyclohexyl-N-methylaminecyclohexanamine (6.83 mL, 29.8 mmol, 1.1 equiv.) in DMF (54 mL) was degassed and stirred under an argon atmosphere for 20 min. Allyl alcohol (2.03 mL, 29.8 mmol, 1.1 equiv.) and bis(dibenzylideneacetone)palladium (0) (156 mg, 0.27 mmol, 0.01 equiv.) were added, followed by 2-(tert-butylphosphino)-1-phenyl-1H-indole (274 mg, 0.81 mmol, 0.03 equiv.) and the reaction was heated to 100° C. for 1 h. After cooling down to r.t., it was diluted with ether and washed three times with water. The organic layer was dried over sodium sulfate and the solvent was evaporated. The residue (GC ratio of linear/branched products: 25:1) was purified by flash column chromatography on silica gel (Heptane/AcOEt 65:35) and bulb-to-bulb distillation (0.15 mbar, 140-145° C.) to afford the desired aldehyde as an oil (3.56 mg, 60% yield).
$^1$H NMR: 1.31 (s, 6H), 2.32 (s, 3H), 2.73 (dt, J=7.7, 1.2 Hz, 2H), 2.91 (d, J=7.7 Hz, 2H), 3.58 (s, 2H), 7.09 (m, 1H), 7.15 (m, 2H), 9.84 (t, J=1.2 Hz, 1H).
$^{13}$C NMR: 201.7 (d), 144.5 (s), 136.2 (s), 135.8 (s), 128.6 (d), 128.3 (d), 124.1 (d), 73.0 (t), 43.9 (t), 39.7 (s), 25.4 (q, 2C), 24.9 (t), 19.6 (q).

Example 2

Preparation of a Perfuming Composition
A woman's perfume, was prepared by admixing the following ingredients:

| Ingredients | Part by weight |
| --- | --- |
| Benzyl acetate | 60 |
| Ethyl 3-oxobutanoate and (2Z)-ethyl 3-hydroxy-2-butenoate | 20 |
| Allyl (3-methylbutoxy)acetate and (+−)-allyl (2-Methylbutoxy)acetate | 20 |
| (−)-(3aR,5aS,9aS,9bR)-3a,6,6,9a-tetramethyldodecahydronaphtho[2,1-b]furan | 20 |
| 10%* (+−)-ethyl 2-methylpentanoate | 20 |
| 7-methyl-2H-1,5-benzodioxepin-3(4H)-one | 20 |
| Cassis base | 120 |

-continued

| Ingredients | Part by weight |
|---|---|
| 3-methyl-2-[(2Z)-2-penten-1-yl]-2-cyclopenten-1-one | 40 |
| (+−)-3,7-dimethyl-6-octen-1-ol | 100 |
| Allyl (cyclohexyloxy)acetate | 10 |
| 10%* (2e)-1-(2,6,6-trimethyl-1,3-cyclohexadien-1-yl)-2-buten-1-one | 60 |
| (+−)-4-decanolide | 20 |
| 10%* (+−)-(e)-8-decen-5-olide and (+−)-(Z)-8-decen-5-olide | 20 |
| (+−)-2,6-dimethyl-7-octen-2-ol | 80 |
| Dipropylene glycol | 800 |
| 10%* 1-methoxy-4-(2-propen-1-yl)benzene | 40 |
| (Z)-3,7-dimethyl-1,6-nonadien-3-ol and (E)-3,7-dimethyl-1,6-nonadien-3-ol | 400 |
| (+−)-3-(3-isopropyl-1-phenyl)butanal | 20 |
| (+−)-4,6,6,7,8,8-hexamethyl-1,3,4,6,7,8-Hexahydrocyclopenta[g]isochromene | 1000 |
| (E)-3,7-dimethyl-2,6-octadien-1-ol | 300 |
| 10%* methyl 2-octynoate | 20 |
| Methyl 2-((1RS,2RS)-3-oxo-2-pentylcyclopentyl)acetate | 1000 |
| Methyl dihydrojasmonate with high amount of isomer cis | 1000 |
| (+−)-3-(1,3-benzodioxol-5-yl)-2-methylpropanal | 600 |
| (+−)-7-hydroxy-3,7-dimethyloctanal | 200 |
| 10%* indole | 40 |
| 10%* 2-methoxy-4-[(1e)-1-propen-1-yl]phenol | 20 |
| (+−)-2-methyl-3-[4-(2-methyl-2-propanyl)phenyl]propanal | 1000 |
| (+−)-3,7-dimethyl-1,6-octadien-3-ol | 200 |
| (+−)-2,6-dimethyl-5-heptenal | 20 |
| (+−)-(E)-3-methyl-4-(2,6,6-trimethyl-2-cyclohexen-1-yl)-3-buten-2-one | 400 |
| (+−)-3-methylcyclopentadecanone | 400 |
| 10%* (2RS,4SR)-4-methyl-2-(2-methyl-1-propen-1-yl)tetrahydro-2H-Pyran and (2RS,4RS)-4-methyl-2-(2-methyl-1-propen-1-yl)tetrahydro-2H-pyran | 10 |
| 2-phenylethanol | 100 |
| 10%* (Z)-3-hexen-1-ol | 80 |
| Orange oil | 10 |
| (3Z)-3-hexen-1-yl salicylate | 200 |
| (+−)-3-methyl-5-(2,2,3-trimethyl-3-cyclopenten-1-yl)-2-pentanol | 60 |
| (+−)-1-(3,5,5,6,8,8-hexamethyl-5,6,7,8-tetrahydro-2-naphthalenyl)ethanone | 600 |
| (+−)-(E)-4-methyl-3-decen-5-ol | 800 |
| (1RS,2RS)-2-(2-methyl-2-propanyl)cyclohexyl acetate and (1RS,2SR)-2-(2-methyl-2-propanyl)cyclohexyl acetate | 60 |
| 2,4-dimethyl-3-cyclohexene-1-carbaldehyde | 10 |
|  | 10000 |

*in dipropyleneglycol

The addition of 800 parts by weight of 3-(4-(1-hydroxy-2-methylpropan-2-yl)phenyl)propanal obtained in example 1 to replace 800 parts by weight of dipropylene glycol to the above-described composition imparted to the latter a floral muguet note in the direction of Lyral® while conferring in addition a creamier and powdery aspect. When instead of the invention's compound, the same amount of 3-[4-(2-hydroxy-2-methylpropyl)phenyl]propanal was used to replace 800 parts by weight of dipropylene glycol, the composition acquired a remarkable radiance, and volume associated with a floral, wetty twist very close to the one obtained when instead of 3-[4-(2-hydroxy-2-methylpropyl)phenyl]propanal was added Lyral®.

Lyral® and 3-[4-(2-hydroxy-2-methylpropyl)phenyl]propanal blend well with the ozone, watery and salicylate notes of the perfuming composition whereas 3-(4-(1-hydroxy-2-methylpropan-2-yl)phenyl)propanal blends particularly well with the salicylate and musky notes.

Example 3

Preparation of a Perfuming Composition

A men's perfume was prepared by admixing the following ingredients:

| Ingredients | Part by weight |
|---|---|
| 1,1-dimethyl-2-phenylethyl acetate | 160 |
| (+−)-1,5-dimethyl-1-vinyl-4-hexenyl acetate | 160 |
| (+−)-1-phenylethyl acetate | 20 |
| 1%* hexyl acetate | 40 |
| (2E)-2-benzylideneoctanal | 160 |
| (−)-(3aR,5aS,9aS,9bR)-3a,6,6,9a-tetramethyldodecahydronaphtho[2,1-b]furan | 80 |
| 1%* methyl 2-aminobenzoate | 40 |
| 10%* (Z)-3,7-dimethyl-2,6-octadienal and (E)-3,7-dimethyl-2,6-octadienal | 40 |
| (+−)-3,7-dimethyl-6-octen-1-ol | 40 |
| 2-chromenone | 40 |
| Allyl (cyclohexyloxy)acetate | 20 |
| 10%* (+−)-(2E)-1-(2,6,6-trimethyl-2-cyclohexen-1-yl)-2-buten-1-one | 80 |
| (+−)-2,6-dimethyl-7-octen-2-ol | 400 |
| Dipropylene glycol | 800 |
| 3-(4-ethylphenyl)-2,2-dimethylpropanal and 3-(2-ethylphenyl)-2,2-dimethylpropanal | 40 |
| (+−)-4,6,6,7,8,8-hexamethyl-1,3,4,6,7,8-hexahydrocyclopenta[g]isochromene | 4600 |
| (E)-3,7-dimethyl-2,6-octadien-1-ol | 40 |
| Geranium rose oil | 40 |
| methyl 2-((1RS,2RS)-3-oxo-2-pentylcyclopentyl)acetate | 400 |
| (+−)-3-(1,3-benzodioxol-5-yl)-2-methylpropanal | 300 |
| 1-(octahydro-2,3,8,8-tetramethyl-2-naphtalenyl)-1-ethanone | 600 |
| Lavandin oil | 40 |
| (+−)-2-methyl-3-[4-(2-methyl-2-propanyl)phenyl]propanal | 800 |
| Methyl 2,4-dihydroxy-3,6-dimethylbenzoate | 80 |
| 10%* (2E,6Z)-2,6-nonadienal | 40 |
| 2-Methylbutyl salicylate and pentyl salicylate | 40 |
| (3Z)-3-hexen-1-yl salicylate | 40 |
| (+−)-3-methyl-5-(2,2,3-trimethyl-3-cyclopenten-1-yl)-2-pentanol | 400 |
| (+−)-1-(3,5,5,6,8,8-hexamethyl-5,6,7,8-tetrahydro-2-naphthalenyl)ethanone | 400 |
| 10%* (2E)-2-hexenal | 20 |
| 10%* 2,4-Dimethyl-3-cyclohexene-1-carbaldehyde | 40 |
|  | 10000 |

*in dipropyleneglycol

The addition of 800 parts by weight of 3-(4-(1-hydroxy-2-methylpropan-2-yl)phenyl)propanal obtained in example 1 to replace 800 parts by weight of dipropylene glycol to the above-described composition imparted to the latter a floral muguet note in the direction of Lyral® while conferring in addition a creamier and powdery aspect.

When instead of the invention's compound, the same amount of 3-[4-(2-hydroxy-2-methylpropyl)phenyl]propanal was used to replace 800 parts by weight of dipropylene glycol, the composition acquired a remarkable radiance, and volume associated with a floral, wetty twist very close to the one obtained when instead of 3-[4-(2-hydroxy-2-methylpropyl)phenyl]propanal was added Lyral®.

Lyral® and 3-[4-(2-hydroxy-2-methylpropyl)phenyl]propanal blend well with the ozone, watery, salicylate and oak moss notes of the perfuming composition whereas 3-(4-(1-hydroxy-2-methylpropan-2-yl)phenyl)propanal blends particularly well with the salicylate and musky notes.

Example 4

Preparation of a Perfume Comprising the Invention's Composition

The perfume was prepared by adding 5 to 15% by weight, relative to the total weight of the perfume, of the invention's composition of example 2 or 3 into ethanol under gentle shaking.

The invention claimed is:

1. A method to confer, enhance, improve or modify odor properties of a perfuming composition or of a perfumed article, the method comprising adding to said composition or article an effective amount of a compound of formula (I) use as a perfuming ingredient, wherein formula (I) is:

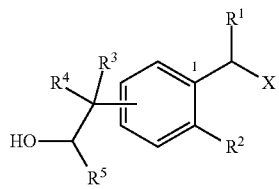
(I)

in the form of any one of its stereoisomers or a mixture thereof, and wherein

X represents a CHO group when $R^1$ represents a $C_{1-2}$ alkyl group or X represents a $CH(R^6)CHO$ group when $R^1$ represents a hydrogen atom or a $C_{1-2}$ alkyl group;

each $R^2$, $R^3$, $R^4$, $R^5$ and $R^6$ represents, independently from each other, a hydrogen atom or a $C_{1-2}$ alkyl group; or $R^3$ and $R^4$ represent, when taken together, an ethanediyl group; and —$C(R^3)(R^4)$—$CH(R^5)$—OH group is, relative to position 1, an ortho, a meta, a para substituent of the aromatic ring or a mixture thereof.

2. The method according to claim 1, characterized in that the —$C(R^3)(R^4)$—$CH(R^5)$—OH group is a meta or para substituent of the aromatic ring, relative to position 1.

3. The method according to claim 1, characterized in that the compound (I) is a compound of formula II

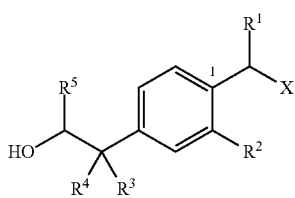
(II)

in the form of any one of its stereoisomers or a mixture thereof, and wherein X, $R^1$, $R^2$, $R^3$, $R^4$, $R^5$, and $R^6$ have the same meaning as defined in claim 1.

4. The method according to claim 1, characterized in that $R^1$ is a methyl group when X represents a CHO group or $R^1$ is a hydrogen atom or a methyl group when X represents a $CH(R^6)CHO$ group, $R^6$ having the same meaning as defined in claim 1.

5. The method according to claim 1, characterized in that the compound (I) is a compound of formula (III)

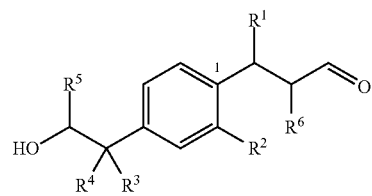
(III)

in the form of any one of its stereoisomers or a mixture thereof, and wherein $R^1$, $R^2$, $R^3$, $R^4$, $R^5$, and $R^6$ have the same meaning as defined in claim 1.

6. The method according to claim 1, characterized in that $R^2$, $R^5$, and $R^6$ is a hydrogen atom or a methyl group.

7. The method according to claim 1, characterized in that $R^3$ is a methyl group and $R^4$ may be a hydrogen atom or a methyl group or $R^3$ and $R^4$ represent, when taken together, an ethanediyl group.

8. The method according to claim 1, characterized in that the compound (I) is a compound of formula IV

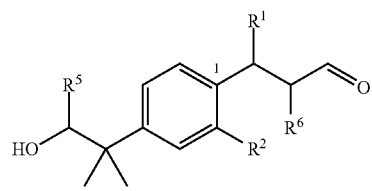
(IV)

in the form of any one of its stereoisomers or a mixture thereof, and wherein $R^1$, $R^2$, $R^5$, and $R^6$ have the same meaning as defined in claim 1.

9. The method according to claim 8, characterized in that $R^1$, $R^2$, $R^5$, and $R^6$ represent, independently from each other, a hydrogen atom.

10. A compound of formula (I) as defined in claim 1 provided that 3-(4-(1-hydroxy-2-methylpropan-2-yl)phenyl)propanal, 3-(4-(2-hydroxyethyl)phenyl)propanal, 3-(4-(1-(hydroxymethyl)cyclopropyl)phenyl)propanal, 3-(4-(1-hydroxy-2-methylpropan-2-yl)phenyl)butanal, 3-(4-(2-hydroxypropyl)phenyl)propanal, 3-(4-(1-(hydroxymethyl)cyclopropyl)phenyl)butanal, 3-(3-(1-(hydroxymethyl)cyclopropyl)phenyl)butanal, 3-(3-(1-(hydroxymethyl)cyclopropyl)phenyl)propanal, 3-(2-(1-(hydroxymethyl)cyclopropyl)phenyl)propanal, 3-(2-(1-(hydroxymethyl)cyclopropyl)phenyl)butanal, 3-(3-(2-hydroxypropyl)phenyl)butanal, 3-(3-(2-hydroxypropyl)phenyl)propanal, 3-(3-(2-hydroxyethyl)phenyl)propanal, 3-(3-(2-hydroxyethyl)phenyl)butanal, 3-(3-(1-hydroxy-2-methylpropan-2-yl)phenyl)butanal, 3-(3-(1-hydroxy-2-methylpropan-2-yl)phenyl)propanal, 3-(2-(1-hydroxy-2-methylpropan-2-yl)phenyl)propanal, 3-(2-(1-hydroxy-2-methylpropan-2-yl)phenyl)butanal, 3-(2-(2-hydroxypropyl)phenyl)butanal, 3-(2-(2-hydroxypropyl)phenyl)propanal, 3-(4-(2-hydroxyethyl)phenyl)butanal and 3-(4-(2-hydroxypropyl)phenyl)butanal are excluded.

11. A perfuming composition comprising:
i) at least one compound of formula (I), as defined in claim 1;
ii) at least one ingredient selected from the group consisting of a perfumery carrier and a perfumery base; and
optionally at least one perfumery adjuvant.

12. A perfumed consumer product comprising at least one compound of formula (I), as defined in claim 1.

13. The perfumed consumer product according to claim 12, characterized in that the perfumed consumer product is a perfume, a fabric care product, a body-care product, a cosmetic preparation, a skin-care product, an air care product or a home care product.

14. The perfumed consumer product according to claim 13, characterized in that the perfumed consumer product is a fine perfume, a splash or eau de parfum, a cologne, a shave or after-shave lotion, a liquid or solid detergent, a fabric softener, a fabric refresher, an ironing water, a paper, a bleach, a carpet cleaner, a curtain-care product, a shampoo, a coloring preparation, a color care product, a hair shaping product, a dental care product, a disinfectant, an intimate care product, a hair spray, a vanishing cream, a deodorant or antiperspirant, a hair remover, a tanning or sun product, a nail product, a skin cleansing, a makeup, a perfumed soap, a shower or bath mousse, an oil or gel, a foot/hand care product, a hygiene product, an air freshener, a "ready to use" powdered, an air freshener, a mold remover, a furnisher care, a wipe, a dish detergent or a hard-surface detergent, a leather care product, a car care product.

15. A perfumed consumer product comprising at least the composition as defined in claim 11.

16. The perfumed consumer product according to claim 15, characterized in that the perfumed consumer product is a perfume, a fabric care product, a body-care product, a cosmetic preparation, a skin-care product, an air care product or a home care product.

17. The perfumed consumer product according to claim 16, characterized in that the perfumed consumer product is a fine perfume, a splash or eau de parfum, a cologne, a shave or after-shave lotion, a liquid or solid detergent, a fabric softener, a fabric refresher, an ironing water, a paper, a bleach, a carpet cleaner, a curtain-care product, a shampoo, a coloring preparation, a color care product, a hair shaping product, a dental care product, a disinfectant, an intimate care product, a hair spray, a vanishing cream, a deodorant or antiperspirant, a hair remover, a tanning or sun product, a nail product, a skin cleansing, a makeup, a perfumed soap, a shower or bath mousse, an oil or gel, a foot/hand care product, a hygiene product, an air freshener, a "ready to use" powdered, an air freshener, a mold remover, a furnisher care, a wipe, a dish detergent or a hard-surface detergent, a leather care product, a car care product.

* * * * *